United States Patent [19]

Hutmacher et al.

[11] Patent Number: 4,730,041

[45] Date of Patent: Mar. 8, 1988

[54] PREPARATION OF ε-CAPROLACTAMS

[75] Inventors: Hans-Martin Hutmacher, Ludwigshafen; Franz Merger, Frankenthal; Franz J. Broecker, Ludwigshafen; Rolf Fischer, Heidelberg; Uwe Vagt, Speyer; Wolfgang Harder, Weinheim; Claus-Ulrich Priester, Meckenheim; Heinz-Walter Schneider, Ludwigshafen; Wolfgang Richter, Wachenheim, all of Fed. Rep. of Germany

[73] Assignee: BASF Aktiengesellschaft, Ludwigshafen, Fed. Rep. of Germany

[21] Appl. No.: 7,789

[22] Filed: Jan. 28, 1987

[30] Foreign Application Priority Data

Jan. 28, 1986 [DE] Fed. Rep. of Germany ....... 3602376

[51] Int. Cl.$^4$ ............................................ C07D 201/08
[52] U.S. Cl. .................................................... 540/538
[58] Field of Search ......................................... 540/538

[56] References Cited

FOREIGN PATENT DOCUMENTS 43-29148 12/1968 Japan .................................... 540/538
1132776 11/1968 United Kingdom ................ 585/752
1191539 5/1970 United Kingdom ................ 540/538

Primary Examiner—Robert T. Bond
Attorney, Agent, or Firm—Keil & Weinkauf

[57] ABSTRACT

Caprolactam is prepared by a process in which (a) a 5-formylvalerate is reacted with excess ammonia and hydrogen in the presence of an alkanol as a solvent and in the presence of a hydrogenation catalyst under superatmospheric pressure in the liquid phase at from 40° to 130° C., (b) excess ammonia and hydrogen are separated off from the reaction mixture and (c) the reaction mixture thus obtained is heated to 150°–250° C. and ε-caprolactam is obtained.

9 Claims, No Drawings

PREPARATION OF ε-CAPROLACTAMS

The present invention relates to a process for the preparation of ε-caprolactam from 5-formylvalerates. British patent No. 1,191,539 describes a process for the preparation of ε-caprolactam, in which 5-formylvalerates are reacted with hydrogen, ammonia and steam in the gas phase at 260° C. in the presence of a copper catalyst. However, difficulties are encountered in connection with the poor vaporizability of the thermally unstable 5-formylvalerate and with the insufficient catalysts lives. Furthermore, Japanese patent publication No. 29148/1968 discloses that 5-formylvalerates can be reacted with ammonia in the presence of water at 230° C. and under 150 bar and in the presence of Raney nickel in the liquid phase. This process has the disadvantage that the yields fluctuate very greatly when the process is carried out industrially.

It is an object of the present invention to provide a process for the preparation of ε-caprolactam starting from 5-formylvalerates the said process giving high yields and producing very little by-product.

We have found that this object is achieved by a process for the preparation of ε-caprolactam by reacting the 5-formylvalerate with excess ammonia and hydrogen in the presence of a hydrogenation catalyst and of a solvent at elevated temperatures and under superatmospheric pressure in the liquid phase, wherein
(a) a 5-formylvalerate is reacted with excess ammonia and hydrogen in the presence of an alkanol as a solvent and in the presence of a hydrogenation catalyst under superatmospheric pressure in the liquid phase at from 40° to 130° C.,
(b) excess ammonia and hydrogen are separated off from the reaction mixture and
(c) the reaction mixture thus obtained is heated to 150°–250° C. and ε-caprolactam is obtained.

The novel process has the advantage that it gives high yields and only a small amount of by-products is formed.

The novel process is noteworthy in that, as demonstrated in Japanese Patent Publication No. 29148/1968, the use of solvents such as dioxane instead of water results in the formation of substantial amounts of by-products and a considerable reduction in the yield.

Preferred 5-formylvalerates are alkyl 5-formylvalerates, in particular those of $C_1$–$C_4$-alkanols, such as methyl, ethyl, propyl, isopropyl or n-butyl esters. Accordingly, suitable starting compounds are methyl 5-formylvalerate, ethyl 5-formylvalerate, propyl 5-formylvalerate, isopropyl 5-formylvalerate and n-butyl 5-formylvalerate. Methyl 5-formylvalerate has become particularly important industrially.

The reaction in stage (a) is carried out in the presence of an alkanol, e.g. a $C_1$–$C_4$-alkanol, as the solvent. Advantageously used alkanols are those which correspond to the alcohol component of the 5-formylvalerate. Accordingly, preferred solvents are methanol, ethanol, propanol, isopropanol and n-butanol. The combination methyl 5-formylvalerate/methanol is particularly preferred. Advantageously, the 5-formylvalerates are used as 1–50, preferably 2 to 35, in particular 5–25, % strength by weight solutions in the stated solvents.

In the reaction, ammonia is used in excess, from 2 to 50 moles of ammonia advantageously being employed per mole of 5-formylvalerate. Particularly good results are obtained if from 5 to 30, in particular from 10 to 25, moles of ammonia are employed per mole of 5-formylvalerate.

The reaction is carried out in the liquid phase at from 40° to 130° C., preferably from 40° to 95° C., in particular from 60° to 90° C.

Advantageously, from 1 to 20 moles of hydrogen are used per mole of 5-formylvalerate. It has proven advantageous to maintain a hydrogen partial pressure of from 5 to 1000, preferably from 20 to 500, in particular from 50 to 200, bar.

Preferred hydrogenation catalysts are metals of group VIII of the periodic table, in particular nickel or cobalt catalysts, as well as a noble metal catalysts, such as palladium, platinum or rhodium. The catalysts can be used in the form of solid catalysts, for example in a finely divided form, such as Raney nickel or Raney cobalt, in suspension or magnetically fixed, in the form of mixed catalysts or in the form of a deposit on a carrier. Examples of suitable carriers are alumina, silica gel and magnesium silicates.

Skeleton catalysts are also useful. The catalytic reactive metals are particularly advantageously used in a finely divided form. For this reason, the skeleton catalysts have proven particularly useful.

Particularly preferably used catalysts are those which are prepared by calcining a compound of the formula I

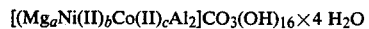

$$[(Mg_a Ni(II)_b Co(II)_c Al_2]CO_3(OH)_{16} \times 4\ H_2O \qquad I$$

where a is an integer or a decimal number from 0 to 4 and b and c are each an integer or a decimal number from 0 to 6, with the proviso that 2 (a+b+c)=12, at from 200° to 600° C. and then reducing the product with hydrogen at elevated temperatures, e.g. from 350° to 400° C. Catalysts which have proven particularly useful are those obtained by calcination and reduction of compounds of the following formulae

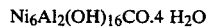

$Ni_6Al_2(OH)_{16}CO.4\ H_2O$

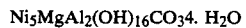

$Ni_5MgAl_2(OH)_{16}CO_3.4\ H_2O$

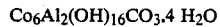

$Co_6Al_2(OH)_{16}CO_3.4\ H_2O$

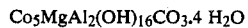

$Co_5MgAl_2(OH)_{16}CO_3.4\ H_2O$

The compounds of the formula I are obtained, for example, as follows: Nickel, aluminum, cobalt and magnesium, in the form of their water-soluble salts, such as chlorides, sulfates or, preferably, nitrates, are dissolved together in water, in a ratio which corresponds very closely to the desired composition of the catalyst and conforms to formula I in its stoichiometry.

The overall molarity of the metal salt solution with respect to metal ions should be 0.5–3, preferably 1.0–2. The metal salt solution is heated to 50°–100° C., preferably 100° C., and combined, in the course of from 0.5 to 10, preferably 3, minutes, with an equivalent amount or preferably a slight excess of a 1–3, preferably 1.5–2.5, molar solution of an alkali metal bicarbonate, this solution having been heated to 50°–100° C., preferably 80°–100° C. Advantageously, the alkali metal bicarbonate is used an excess of up to 20, preferably from 0.5 to 3, % by weight, based on the theoretical amount of bicarbonate. After the addition of the metal salt solution, stirring is advantageously carried out for a further 10–30, preferably 15–25, minutes, after which the resulting precipitate is filtered off, washed with water and dried at from 50° to 200° C., preferably from 100° to 160° C. The basic carbonates are obtained in virtually quantitative yields. Particularly suitable alkali metal bicarbonates are sodium bicarbonate and potassium bicarbonate. However, it is also possible to use ammonium bicarbonate for the precipitation. Of course, mixtures of the stated bicarbonates may also be employed. Moreover, it is possible to precipitate the metal ions using solutions of alkali metal carbonates, such as sodium carbonate and/or potassium carbonate, if carbon dioxide is passed into the initially taken alkali metal carbonate solution during the precipitation; in the end, this amounts to precipitation with a bicarbonate. Calcination is advantageously carried out at from 250° to 400° C. for, for example, from 5 to 40, in particular from 15 to 30, hours. Before the catalyst is actually used, it is advantageous to reduce it with hydrogen at from 180° to 500° C., preferably from 250° to 450° C., in the course of from 5 to 100, advantageously from 10 to 25, hours.

Other preferred catalysts are nickel catalysts which contain nickel in finely divided form applied on a carrier, in particular magnesium silicate. Such catalysts advantageously contain nickel in an amount of from 30 to 60% by weight, based on the total catalyst material including the carrier. Catalysts of this type are described, for example, in German patent No. 1,545,428.

Raney nickel or Raney cobalt is preferably used as the catalyst, these catalysts being employed in suspension or being fixed in the reaction zone on permanent magnets or on soft iron elements in a magnetic or electromagnetic field. Such magnets are arranged, for example, in the form of rods in the reaction zone.

In the reaction, it has also proven advantageous to maintain a residence time of from 1 to 30 minutes and a space velocity of from 0.2 to 2.0 kg of 5-formylvalerate per liter catalyst per hour.

The reaction can be carried out batchwise, for example in a high pressure vessel, but is preferably effected continuously, for example in pressure-tight stirred containers, for example a stirred cascade. It has proven advantageous to avoid batch-mixing during the reaction. For this reason, tube reactors in which the alcoholic solution of the 5-formylvalerate and ammonia is passed over a fixed-bed catalyst have proven particularly useful. The liquid phase procedure has proven suitable for this purpose. After let-down, during which the hydrogen is removed, the reacted mixture obtained from stage a comprises a mixture of 6-aminocarboxylates, the alkanol used, excess ammonia and minor amounts of ε-caprolactam.

Where methyl 5-formylvalerate is used and methanol is employed as the solvent, the resulting reaction mixture consists of methyl 6-aminocaproate in methanol and contains from 1 to 10 mole %, based on methyl 6-aminocaproate and ammonia, of caprolactam.

In a second stage b, the excess ammonia is removed from the reaction mixture. This is done, for example, by distillation or by stripping with an inert gas. The amounts of ammonia and excess hydrogen obtained are advantageously recycled to stage a. It has proven particularly useful to maintain an ammonia content of from 0.1 to 2, in particular from 0.1 to 1, % by weight in the solution to be used further.

The resulting reaction mixture which has been freed from ammonia is heated to 150°–250° C., preferably 170°–230° C., in the subsequent stage c. The pressure maintained is advantageously greater than or equal to the resulting pressure of the reaction mixture and the temperature employed. Residence times of from 0.5 to 5 hours are advantageously maintained, depending on the type of ester used and on the reaction temperatures.

The reaction can be carried out batchwise or, preferably, continuously, for example in high pressure vessels arranged as a cascade, or in tube reactors.

Caprolactam can be isolated from the resulting alcoholic solution of caprolactam in a conventional manner, for example by distillation or extraction. The alcohol used as the solvent, and any unconverted 6-aminocaproate present, can be recycled to stage a or c.

Caprolactam is used for the production of nylon 6.

The Examples which follow illustrate the process according to the invention.

EXAMPLE 1

Stage (a):

A vertical tube reactor having a diameter of 16 mm and a charge height of 25 cm and possessing an oil-heated double jacket was charged with 50 ml of a nickel catalyst containing 55% by weight of finely divided nickel oxide on magnesium silicate, in the form of extrudates of 1.5 mm diameter. The catalyst was reduced in the course of 18 hours, the temperature being increased stepwise from 60° to 330° C. and the hydrogen content of the nitrogen/hydrogen mixture used for reduction being increased from 5 to 50%.

Thereafter, 99.5 g/hour of 10.0% strength by weight methanolic methyl 5-formylvalerate solution and 16.2 g/hour of liquid ammonia were pumped through the reactor from below at 80° C. and under 100 bar, while hydrogen was simultaneously passed through. The reaction mixture passed from the top of the reactor via a condensor into a separator, from where the reacted mixture and 25 hour of waste gas were removed.

Stage (b):

The reacted mixture was brought continuously to the top of a 40 cm long column (stripper) heated to 40° C. and filled with $V_2A$ stainless steel wire mesh rings ($\phi$ 3 mm), 22 hour of nitrogen being blown counter current through the column. 91.2 g/hour of stripped reacted mixture containing 0.5% by ammonia were obtained at the bottom of the column; according to quantitative gas chromatographic analysis, this mixture contained 9.43% of a methyl 6-aminocaproate and 0.36% of caprolactam, corresponding to yields of 86.0% of methyl 6-aminocaproate and 4.2% of caprolactam, the percentages being based on methyl 5-formylvalerate employed.

Stage (c):

A bleed stream of 18.3 g/hour of this reacted mixture was pumped continuously under 105 bar through a reactor having a length of 8.71 m and a diameter of 3.17 mm (coiled tube) and heated at 225° C. At the reactor exit, the reaction mixture was cooled to room temperature and let down to atmospheric pressure, after which is was shown by quantitative gas chromatographic analysis to contain 6.47% of caprolactam and 0.78% of methyl 6-aminocaproate. This corresponds to yields of 75.6% of caprolactam and 7.1% of methyl 6-aminocaproate, the percentages being based on the methyl 5-formylvalerate employed in the hydrogenation stage.

EXAMPLE 2

A rod having a diameter of 9 mm and to which permanent magnets (having a field strength of 500 cm) were fastened was arranged centrally in a vertical tube reactor having a diameter of 14 mm and a length of 450 mm. The magnets were laden with 11.0 g of Raney nickel by passing a suspension of Raney nickel in water through the reactor from below.

Thereafter, 77.3 g/hour of a 12.0% strength by weight methanolic solution of methyl 5-formylvalerate and 24 ml/hour of liquid ammonia were pumped through the reactor below, while 8.7 hour of hydrogen were simultaneously passed through at 76° C. and under 80 bar. The reaction mixture passed from the top of the reactor via a pressure regulating valve to the top of a column (stage 3) which was heated at 40° C. at a length of 40 cm and was filled with V$_2$A stainless steel wire mesh rings ($\phi$ 3 mm) and through which 22 l/hour of nitrogen were blown countercurrent. 72.3 g/hour of stripped reacted mixture containing 0.5% by weight of ammonia were obtained at the bottom of the column; according to quantitative gas chromatographic analysis, the said reacted mixture contained 9.35% of methyl 6-aminocaproate and 0.25% of caprolactam, corresponding to yields of 89.1% of methyl 6-aminocaproate and 3.1% of caprolactam, the percentages being based on methyl 5-formylvalerate used.

Stage c was carried out similarly to Example 1. The yield of caprolactam was 78%.

We claim:

1. A process for the preparation of $\epsilon$-caprolactam, wherein
    (a) a $C_1$-$C_4$-alkyl 5-formylvalerate is reacted with excess ammonia and hydrogen in the presence of an alkanol as a solvent and in the presence of a hydrogenation catalyst under superatmospheric pressure in the liquid phase at from 40° to 130° C.,
    (b) excess ammonia and hydrogen are separated off from the reaction mixture and
    (c) the reaction mixture thus obtained is heated to 150°–250° C. and $\epsilon$-caprolactam is obtained.

2. A process as defined in claim 1, wherein the catalyst used is prepared by calcining a compound of the formula I $$[(Mg_aNi(II)_bCo(II)_c)Al_2]CO_3(OH)_{16} \times 4\ H_2O$$

where a is an integer or decimal number from 0 to 4 and b and c are each an integer or decimal number from 0 to 6, with the proviso that 2 (a+b+c)=12, at from 200° to 600° C. and then reducing the product with hydrogen at elevated temperatures.

3. A process as defined in claim 1, wherein a nickel catalyst which contains from 30 to 60% by weight of nickel deposited in finely divided form or magnesium silicate is used.

4. A process as defined in claim 1, wherein the $C_1$-$C_4$-alkyl 5-formylvalerate in solution with an alkanol and ammonia is passed over a fixed bed catalyst by the liquid phase procedure.

5. A process as defined in claim 1, wherein Raney nickel or Raney cobalt is used in a liquid phase procedure.

6. A process as defined in claim 1, wherein Raney nickel or Raney cobalt is fixed magnetically or electromagnetically in the reaction zone.

7. A process as defined in claim 1, wherein a residence time of from 1 to 30 minutes is maintained in stage a.

8. A process as defined in claim 1, wherein the space velocity maintained is from 0.2 to 2.0 kg of $C_1$-$C_4$-alkyl 5-formylvalerate per liter of catalyst per hour.

9. A process as defined in claim 1, wherein methyl 5-formylvalerate dissolved in methanol is used.

* * * * *